United States Patent [19]

Hay

[11] 4,210,668
[45] Jul. 1, 1980

[54] INSECTICIDAL CARBAMATES
[75] Inventor: James V. Hay, Newark, Del.
[73] Assignee: E. I. Du Pont de Nemours and Company, Wilmington, Del.
[21] Appl. No.: 14,534
[22] Filed: Feb. 23, 1979
[51] Int. Cl.² .................. A01N 9/12; C07C 119/06
[52] U.S. Cl. ..................... 424/298; 260/453 RW
[58] Field of Search ............... 260/453 RW; 424/298
[56] References Cited
FOREIGN PATENT DOCUMENTS 848911 5/1977 Belgium ........................ 260/453 RW
848913 5/1977 Belgium ........................ 260/453 RW
855928 12/1977 Belgium ........................ 260/453 RW
2155392 11/1971 Fed. Rep. of Germany ... 260/453 RW Primary Examiner—John M. Ford
Assistant Examiner—Robert C. Whittenbaugh

[57] ABSTRACT

Insecticidal and nematicidal carbamates such as 2-[N-methyl-N-[N-methyl-N-[(1-methylthioethylidene)aminooxycarbonyl]aminothio]aminocarbonyloxy]benzoic acid esters and amides exhibit increased residual insecticidal and nematicidal activity and reduced cotton phytotoxicity.

55 Claims, No Drawings

INSECTICIDAL CARBAMATES

BACKGROUND OF THE INVENTION

This invention relates to sulfur bridged carbamates useful as insecticides.

German Patent No. 2,155,392, issued Nov. 5, 1971, discloses insecticidal biscarbamoyl sulfides of the formula

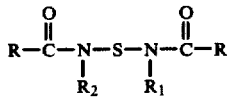

wherein $R_1$ and $R_2$ are $C_1$–$C_4$ alkyl or H; and

R is an aryl group optionally substituted with halogen, nitro, $C_1$–$C_7$ alkyl, $C_1$–$C_5$ alkoxy, $C_1$–$C_3$ alkylmercapto or $C_1$–$C_3$ dialkylamino.

Belgian Patent No. 848,911, issued May 31, 1977, discloses insecticidal compounds of the type

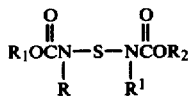

wherein

R and $R^1$ are independently $C_1$–$C_4$ alkyl;
$R_1$ is among others,

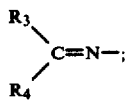

$R_2$ is alkyl, cycloalkyl, phenyl alkyl or naphthylalkyl, optionally substituted with halogen, cyano, nitro, alkyl, alkylthio, alkoxy, alkoxy carbonylamino or $R_2$ is alkyl O(alkyl O)—$_n$alkyl.

Belgian Patent No. 848,913, issued May 31, 1977, discloses insecticidal compounds of the formula

wherein

R and $R^1$ are independently $C_1$–$C_4$ alkyl;
$R_1$ is, among others,

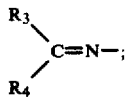

and $R_2$ is alkenyl, alkynyl, or phenyl, optionally substituted with nitro, cyano, alkyl, alkylthio, amino, alkylamino, dialkylamino, alkoxycarbonylamino or alkylcarbonylamino.

Belgian Patent No. 855,928, issued Dec. 21, 1977, discloses insecticidal compounds of the formula

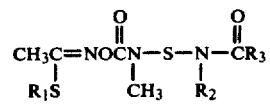

wherein $R_1$ is methyl or ethyl;

$R_2$ is $C_1$–$C_8$ alkyl or $C_3$–$C_8$ cycloalkyl; and $R_3$ is hydrogen, $C_1$–$C_6$ alkoxy or cyclopropyl.

Insect control is an important factor in maintaining adequate and healthy crop growth, since insect infestation can totally destroy or severely diminish food supplies for both man and animal. Additionally, maintenance of general public health is dependent in part on adequate insect control. Thus, since existing products have not been able to completely control the insect population, there is a continuing need for new products having high activity which at the same time do not harm crop growth.

SUMMARY OF THE INVENTION

According to this invention, there are provided compounds of Formula I, suitable insecticidal and nematicidal compositions containing them, and the method of using them as insecticides and nematicides. These compounds exhibit increased residual activity and reduced cotton phytotoxicity.

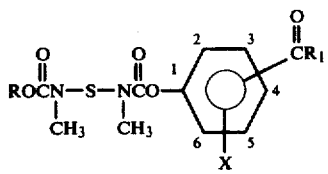

wherein
R is

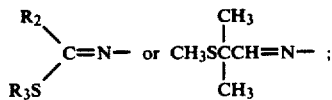

$R_1$ is $OR_4$, $SR_5$ or $NR_6R_7$;
$R_2$ is $C_1$–$C_3$ alkyl, $CH_3OCH_2$— or

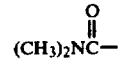

$R_3$ is $C_1$–$C_3$ alkyl;
$R_4$ is $C_1$–$C_{14}$ alkyl, $+CH_2CH_2O+_nR_8$, or $C_6H_5$—;
$R_5$ is $C_1$–$C_4$ aklyl;
$R_6$ and $R_7$ are independently H or $C_1$–$C_3$ alkyl;
$R_8$ is H or $C_1$–$C_3$ alkyl;
X is H, $C_1$–$C_9$ alkyl, Cl, $(CH_3)_2N$ or $OR_9$;
$R_9$ is $C_1$–$C_4$ alkyl;
n is 1, 2 or 3.

Preferred for their great insecticidal or nematicidal activity or favorable cost or both are those compounds of Formula I where independently R is

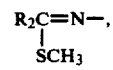

and $R_2$ is $C_1$–$C_3$ alkyl.

More preferred for their greater insecticidal or nematicidal activity or more favorable cost or both are those compounds of Formula I where independently R is

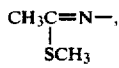

$R_1$ is $OR_4$ and the

group is in the 2-position of the aromatic ring.

Most preferred for their outstanding insecticidal or nematicidal activity or highly favorable cost or both are those compounds of Formula I where independently R is

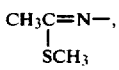

$R_1$ is $OR_4$, $R_4$ is $C_1$–$C_4$ alkyl or —$(CH_2CH_2O)_nR_8$, X is H and

is in the 2-position of the aromatic ring.

The following compounds are specifically preferred for their outstanding insecticidal or nematicidal activity or highly favorable cost or both:
2-[N-methyl-N-[N-methyl-N-[(1-methylthioethylidene)-aminocarbonyl]aminothio]aminocarbonyloxy]benzoic acid butyl ester, and
2-[N-methyl-N-[N-methyl-N-[(1-methylthioethylidene)-aminooxycarbonyl]aminothio]aminocarbonyloxy]benzoic acid methyl ester.

DETAILED DESCRIPTION OF INVENTION

Synthesis

The compounds of Formula I can be prepared, as shown in Equation A, by reacting an appropriate sulfenyl chloride of Formula II with an appropriate carbamate of Formula III, in the presence of an acid acceptor.

Equation A

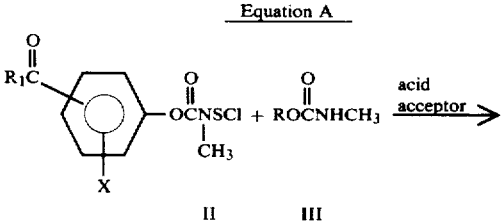

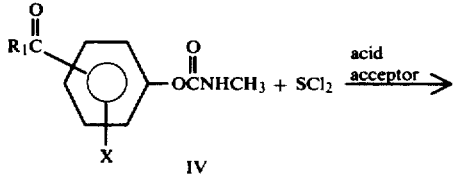

wherein R, $R_1$, and X are as previously defined.

The reaction represented in Equation A may be carried out in an inert organic solvent such as benzene, toluene, the xylenes, ethyl acetate, methylene chloride, chloroform, ethylene dichloride, tetrahydrofuran, dioxane, or dimethyl formamide. Mixtures of these solvents may also be used. The reaction can be performed at temperatures between about −15° and 50° C., preferably between −5° and 30° C. Pressure is not critical for the reaction procedure since pressures above and below atmospheric are suitable. For convenience, atmospheric pressure is preferred.

The acid acceptor used in Equation A can be a tertiary organic amine such as trimethylamine, triethylamine, N,N-dimethylaniline, or pyridine.

The compounds of Formula I obtained via the reaction shown in Equation A may be purified by methods known to those skilled in the art, such as recrystallization, column chromatography, or another suitable procedure.

The sulfenyl chlorides of Formula II used as intermediates in Equation A can be prepared, as shown in Equation B, by reacting a carbamate of Formula IV with a molecular equivalent of sulfur dichloride in the presence of an acid acceptor.

Equation B

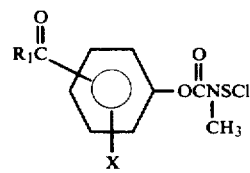

wherein $R_1$ and X are as previously defined.

The reaction shown in Equation B can be carried out in an inert organic solvent such as benzene, toluene, ethyl acetate, methylene chloride, chloroform, or ethylene dichloride. Mixtures of these solvents may be used. The reaction can be carried out at temperatures between about −25° and 15° C., preferably between −10° and 5° C. Pressure is not critical for the reaction procedure since pressures above and below atmospheric are suitable. For convenience, atmospheric pressure is preferred.

The acid acceptor used in Equation B can be a tertiary organic amine such as trimethylamine, triethylamine, N,N-dimethylaniline, or pyridine.

The carbamates of Formula III in Equation A can be prepared by the methods taught in U.S. Pat. Nos. 3,576,384; 3,530,220; and 3,217,037, the disclosures of which are herein incorporated by reference.

The compounds of Formula I can also be prepared, as shown in Equation C, by reacting a phenol of Formula V with a carbamyl fluoride of Formula VI in the presence of an acid acceptor.

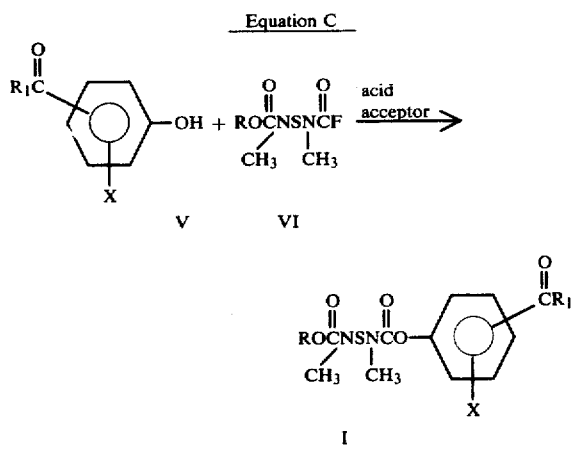

wherein R, R₁, and X are as previously defined.

The reaction shown in Equation C can be carried out in an inert organic solvent such as benzene, toluene, the xylenes, methylene chloride, chloroform, ethylene dichloride, acetone, methyl ethyl ketone, dioxane, tetrahydrofuran, acetonitrile, or dimethyl formamide. Mixtures of these solvents may also be used. The reaction shown in Equation C also may be conducted in a two phase system composed of water, an immiscle, inert organic solvent such as benzene, toluene, the xylenes, methylene chloride, or ethylene dichloride, and a quaternary ammonium salt.

The reaction can be carried out at temperatures between about 0° and 150° C., preferably between 20° and 100° C. Pressure is not critical for the reaction procedure since pressures above or below atmospheric are suitable. For convenience, atmospheric pressure is preferred.

The acid acceptor used in Equation C can be a tertiary organic amine, such as trimethylamine, triethylamine, N,N-dimethylaniline, or pyridine, or inorganic bases, such as the alkali metal and alkaline earth metal hydroxides, carbonates, bicarbonates, hydrides, such as sodium or potassium hydride, and alkoxides, such as sodium methoxide or potassium tert-butoxide.

The compounds of Formula I obtained by the reaction described in Equation C can be purified by methods known to those skilled in the art, such as recrystallization, column chromatography or another suitable procedure.

Carbamyl fluorides used as intermediates in Equation C are known in the art and can be prepared by methods taught in BE Nos. 848,913 and 848,914, the disclosures of which are herein incorporated by reference.

In the following examples, all parts and percentages are by weight and temperatures in degree centigrade unless otherwise specified.

EXAMPLE 1

2-[N-methyl-N-[N-methyl-N-[(1-methylthioethylidene)-aminocarbonyl]aminothio]aminocarbonyloxy]benzoic acid butyl ester A 3.9 g portion of n-butyl salicylate was added dropwise to a stirred suspension of 0.96 g of 50% sodium hydride in mineral oil in 30 ml of dimethylformamide. When the initial vigorous gas evolution subsided, the reaction mixture was warmed on a steam bath until evolution of hydrogen ceased. The reaction solution was cooled to 25° C. after which 5.4 g of methyl N[[N-(fluorocarbonyl-N-methylamino)thio]-N-methylaminocarbonyloxy]]ethanimidothioate was added in one portion. The resulting brown solution was stirred overnight at ambient temperature. The reaction mixture was then poured into 200 ml water, and the aqueous mixture was extracted with ether. The organic solution was washed consecutively with 200 ml of water, 100 ml of 5% sodium hydroxide solution, twice with 200 ml of water, and 100 ml of saturated sodium chloride solution. The organic solution was dried over anhydrous magnesium sulfate, and the solvent was distilled under reduced pressure. The title compound was isolated from the crude reaction product by column chromatography on silica gel, eluting the product with a mixture of ether and hexane (2:1, V/V). Employing this procedure, 2.4 g of 2-[N-methyl-N-[N-methyl-N-[(1-methylthioethylidene)aminooxycarbonyl]aminothio]aminocarbonyloxy]benzoic acid butyl ester was obtained as a viscous yellow oil which solidified on lengthy standing, m.p. 68°-74° C. The product showed absorption bands characteristic of the title compound in the infrared spectrum at 5.95μ and at 0.9–1.9, 2.25, 2.3, 3.5, 3.6, 4.3, 7.0–7.7 and 8.0 ppms by Nuclear Magnetic resonance spectrums.

EXAMPLE 2

2-[N-methyl-N-[N-methyl-N-[(1-methylthioethylidene)aminooxycarbonyl]aminothio]aminocarbonyloxy]benzoic acid butyl ester A 5.8 g portion of n-butyl salicylate was added to a solution of 1.2 g of sodium hydroxide in 75 ml of water, producing a thick suspension. To the above suspension was added 100 ml of methylene chloride and 0.3 g of tricaprylylmethyl ammonium chloride. The reaction mixture was stirred vigorously while a solution of 8.1 g of methyl N-[[N-[(fluorocarbonyl-N-methylamino)thio]-N-methylaminocarbonyloxy]]ethanimidothioate in 50 ml methylene chloride was added dropwise. When addition was complete, stirring was continued for one hour. The organic phase was separated and washed with 200 ml of water followed by 100 ml of saturated sodium chloride solution. The organic solution was dried over anhydrous magnesium sulfate, and the solvent was distilled under reduced pressure. On scratching and standing, the crude reaction product partially solidified. The title compound was isolated by dissolving the crude reaction product in 25 ml of ethanol, cooling the solution and diluting with hexane to afford 5.7 g of 2-[N-methyl-N-[N-methyl-N-[(1-methylthioethylidene)aminooxycarbonyl]aminothio]aminocarbonyloxy]benzoic acid butyl ester, m.p. 87°-89° C. Absorption bands characteristic of the title compound were observed in the infrared and NMR spectrums.

By employing the appropriate procedure as described in Examples 1 and 2, the compounds shown in Tables I-VII can be prepared.

TABLE II

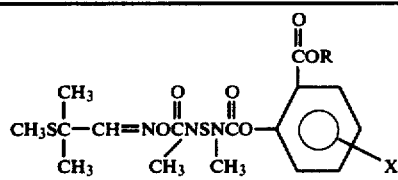

| R | X |
|---|---|
| CH₃ | H |

TABLE I

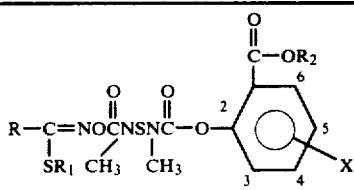

| R | R₁ | R₂ | X | Physical Property |
|---|---|---|---|---|
| CH₃ | CH₃ | CH₃ | H | mp 80°–85° |
| CH₃ | CH₃ | CHCH₃ / CH₃ | H | mp 106°–109° |
| CH₃ | CH₃ | n-C₈H₁₇ | H | mp 57°–64° |
| CH₃ | CH₃ | n-C₁₄H₂₉ | H | mp 50°–52° |
| CH₃ | CH₃ | C₆H₅ | H | mp 128°–134° C. |
| CH₃ | CH₃ | s-C₄H₉ | H | |
| CH₃ | CH₃ | N—C₅H₁₁ | H | |
| CH₃ | CH₃ | CH₂CH(CH₂)₃CH₃ / C₂H₅ | H | |
| CH₃ | CH₃ | CH₂CHCH₃ / CH₃ | H | |
| CH₃ | CH₃ | CH₂CH₂CHCH₃ / CH₃ | H | |
| CH₃ | CH₃ | CH₂CCH₂CHCH₃ / (CH₃)₂ CH₃ | H | |
| CH₃ | CH₃ | N—C₁₀H₂₁ | H | |
| CH₃ | CH₃ | C₁₂H₂₅ | H | |
| CH₃ | CH₃ | CH₂CH₂OH | H | |
| CH₃ | CH₃ | CH₂CH₂OCH₃ | H | |
| CH₃ | CH₃ | CH₂CH₂OC₂H₅ | H | mp 71.5°–73.5° C=O (5.79μ) |
| CH₃ | CH₃ | (CH₂CH₂O)₂C₂H₅ | H | |
| CH₃ | CH₃ | (CH₂CH₂O)₃n-C₃H₇ | H | |
| C₂H₅ | CH₃ | CH₃ | H | |
| n-C₃H₇ | CH₃ | CH₃ | H | |
| CH₃OCH₂ | CH₃ | CH₃ | H | |
| C₂H₅ | n-C₃H₇ | CH₃ | H | |
| n-C₃H₇ | n-C₃H₇ | CH₃ | H | |
| (CH₃)₂NC(O) | CH₃ | CH₃ | H | |
| (CH₃)₂NC(O) | CH₃ | n-C₄H₉ | H | |
| CH₃ | CH₃ | n-C₄H₉ | 3-CH₃ | C=O (5.79μ) |
| CH₃ | CH₃ | n-C₄H₉ | 3-OCH₃ | |
| CH₃ | CH₃ | CH₃ | 3-OCH₃ | C=O (5.80μ) |
| CH₃ | CH₃ | n-C₄H₉ | 4-Cl | |
| CH₃ | CH₃ | n-C₄H₉ | 5-Cl | C=O (5.77μ) |
| CH₃ | CH₃ | CH₃ | 5-Cl | mp 115°–121° |
| CH₃ | CH₃ | n-C₄H₉ | 4-(CH₃)₂N | |
| CH₃ | CH₃ | CH₃ | 4-(CH₃)₂N | mp 125°–127° |
| CH₃ | CH₃ | CH₃ | 5-CH₃O | mp 114°–117° |
| CH₃ | CH₃ | n-C₄H₉ | 5-CH₃O | mp 75°–78° |
| CH₃ | CH₃ | n-C₄H₉ | 5-n-C₄H₉O— | mp 57°–60° |
| CH₃ | CH₃ | CH₃ | 5-n-C₄H₉O | mp 86°–89.5° |
| CH₃ | CH₃ | CH₃ | 4-CH₃O | mp 90°–95° |
| CH₃ | CH₃ | n-C₄H₉ | 4-n-C₄H₉O | mp 107°–109° |
| CH₃ | CH₃ | CH₃ | 5-n-C₄H₉O | mp 79°–82° |

TABLE II-continued $$\text{CH}_3\text{SC}-\overset{\underset{\displaystyle |}{\text{CH}_3}}{\text{CH}}=\text{N}\overset{\text{O}}{\overset{\|}{\text{O}\text{C}}}\overset{\underset{\displaystyle |}{\text{CH}_3}}{\text{N}}\overset{\text{O}}{\overset{\|}{\text{C}\text{O}}}\text{-}\phantom{X}\bigcirc\text{-}_X^{\text{COR}}$$

| R | X |
|---|---|
| n-C$_4$H$_9$ | H |

TABLE III $$R-\overset{\underset{\displaystyle |}{\text{SCH}_3}}{\text{C}}=\text{N}-\overset{\text{O}}{\overset{\|}{\text{OC}}}\overset{\underset{\displaystyle |}{\text{CH}_3}}{\text{N}}\overset{\text{O}}{\overset{\|}{\text{CO}}}\text{-}\bigcirc\text{-}_X^{\text{CSR}_1}$$

| R | R$_1$ | X |
|---|---|---|
| CH$_3$ | CH$_3$ | H |
| CH$_3$ | C$_2$H$_5$ | H |
| CH$_3$ | n-C$_3$H$_7$ | H |
| CH$_3$ | CH$_3$ | H |
| (CH$_3$)$_2$NC(O) | CH$_3$ | |

TABLE IV $$R-\text{C}=\text{NOCNSNCO-}\bigcirc\text{-}_X^{\text{CNR}_6\text{R}_7}$$
(with SCH$_3$, CH$_3$, CH$_3$ substituents)

| R | R$_6$ | R$_7$ | X | Physical Property |
|---|---|---|---|---|
| CH$_3$ | H | H | H | mp 154°–156° |
| CH$_3$ | H | n—C$_3$H$_7$ | H | |
| CH$_3$ | n—C$_3$H$_7$ | n—C$_3$H$_7$ | H | |
| (CH$_3$)$_2$NC(O) | CH$_3$ | CH$_3$ | H | |

TABLE V $$\text{CH}_3\text{SC}-\text{CH}=\text{NOCNSNCO-}\bigcirc\text{-}_X$$
(with CH$_3$, CH$_3$, CH$_3$ substituents)

| R | X |
|---|---|
| SCH$_3$ | H |
| N(CH$_3$)$_2$ | H |

TABLE VI $$R-\text{C}=\text{NOCNSNCO-}\bigcirc\text{-CR}_1$$
(with SCH$_3$, CH$_3$, CH$_3$ substituents)

| R | R$_1$ | Physical Property |
|---|---|---|
| CH$_3$ | OCH$_3$ | mp 142°–144° |
| CH$_3$ | OC$_2$H$_5$ | mp 104° |
| CH$_3$ | On-C$_4$H$_9$ | mp 101°–103° |
| CH$_3$ | SCH$_3$ | |

TABLE VI-continued $$R-\text{C}=\text{NOCNSNCO-}\bigcirc\text{-CR}_1$$

| R | R$_1$ | Physical Property |
|---|---|---|
| (CH$_3$)$_2$NC(O) | OCH$_3$ | |

TABLE VII $$\text{CH}_3\text{SC}-\text{CH}=\text{NOCNSNCO-}\bigcirc\text{-CR}$$
(with CH$_3$, CH$_3$, CH$_3$ substituents)

| R |
|---|
| OCH$_3$ |
| On-C$_4$H$_9$ |
| N(CH$_3$)$_2$ |

FORMULATION

Useful formulations of the compounds of Formula I can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few pints to several hundred gallons per acre. High strength compositions are primarily used as intermediates for further formulation. The formulations, broadly, contain about 1% to 99% by weight of active ingredient(s) and at least one of a) about 0.1% to 20% surfactant(s) and b) about 5% to 99% solid or liquid diluent(s). More specifically, they will contain these ingredients in the following approximate proportions:

| | Percent by Weight | | |
|---|---|---|---|
| | Active Ingredient | Diluent(s) | Surfactant(s) |
| Wettable Powders | 20–90 | 0–74 | 1–10 |
| Oil Suspensions, Emulsions, Solutions (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins et al, "Handbook of Insecticide Dust Diluents and Carriers", 2nd Edn., Dorland Books, Caldwell, N.J. The more absorptive diluents are preferred for wettable powders and the denser ones for dusts. Typical liquid diluents and solvents are described in Marsden, "Solvents Guide", 2nd Edn., Interscience, New York, 1950. Solubility under 0.1% is preferred for suspension concentrates; solution concentrates are preferably stable against phase separation at 0° C. "McCutcheon's Detergents and Emulsifiers Annual", Allured Publ. Corp., Ridgewood, N.J., as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp 147ff. and "Perry's Chemical Engineer's Handbook", 4th Edn., McGraw-Hill, N.Y., 1963, pp. 8–59ff.

For further information regarding the art of formulation, see for example:

J. B. Buchanan, U.S. Pat. No. 3,576,834, April 27, 1971, Col. 5, line 36 through Col. 7, line 70 and Ex. 1–4, 17, 106, 123–140.

R. R. Shaffer, U.S. Pat. No. 3,560,616, Feb. 2, 1971, Col. 3, line 48 through Col. 7, line 26 and Ex. 3–9, 11–18.

E. Somers, "Formulation", Chapter 6 in Torgeson, "Fungicides", Vol. I, Academic Press, New York, 1967.

In the following examples, all parts and percentages are by weight and temperatures in degree centigrade unless otherwise specified.

EXAMPLE 3

| Wettable Powder | |
|---|---|
| 2-[N-methyl-N-[N-methyl-N-[(1-methyl-thioethylidene)aminooxycarbonyl]-aminothio]aminocarbonyloxy]benzoic acid methyl ester | 65% |
| dodecylphenol polyethylene glycol ether | 2% |
| sodium ligninsulfonate | 4% |
| sodium silicoaluminate | 6% |
| montmorillonite (calcined) | 23% |

The ingredients are thoroughly blended. The liquid surfactant is added by spraying upon the solid ingredients in the blender. After grinding in a hammer mill to produce particles essentially all below 100 microns, the material is reblended and sifted through a U.S.S. No. 50 sieve (0.3 mm opening) and packaged.

EXAMPLE 4

| Wettable Powder | |
|---|---|
| 2-[N-methyl-N-[N-methyl-N-[(1-methyl-thioethylidene)aminocarbonyl]amino-thio]aminocarbonyloxy]benzoic acid butyl ester | 50% |
| sodium alkylnaphthalenesulfonate | 2% |
| low viscosity methyl cellulose | 2% |
| diatomaceous earth | 46% |

The ingredients are blended, coarsely hammer-milled and then air milled to produce particles of active essentially all below 10 microns in diameter. The product is reblended before packaging.

EXAMPLE 5

| High Strength Concentrate | |
|---|---|
| 2-[N-methyl-N-[N-methyl-N-[(1-methyl-thioethylidene)aminocarbonyl]amino-thio]aminocarbonyloxy]benzoic acid butyl ester | 98.5% |
| silica aerogel | 0.5% |
| synthetic amorphous fine silica | 1.0% |

The ingredients are blended are ground in a hammer mill to produce a high strength concentrate essentially all passing a U.S.S. No. 50 sieve (0.3 mm openings). This material may then be formulated in a variety of ways.

EXAMPLE 6

| Dust | |
|---|---|
| high strength concentrate, Example 5 | 25.4% |
| pyrophyllite, powdered | 74.6% |

The ingredients are thoroughly blended and packaged for use.

EXAMPLE 7

| Emulsifiable Concentrate | |
|---|---|
| 2-[N-methyl-N-[N-methyl-N-[(1-methyl-thioethylidene)aminooxycarbonyl]amino-thio]aminocarbonyloxy]benzoic acid methyl ester | 10% |
| blend of oil soluble sulfonates and polyoxyethylene ethers | 4% |
| xylene | 86% |

The ingredients are combined and stirred with gentle warming to speed solution. A fine screen filter is included in packaging operation to insure the absence of any extraneous undissolved material in the product.

EXAMPLE 8

| Granule | |
|---|---|
| wettable powder of Example 4 | 16% |
| gypsum | 68% |
| potassium sulfate | 16% |

The ingredients are blended in a rotating mixer and water sprayed on to accomplish granulation. When most of the material has reached the desired range of 1.0 to 0.42 mm (U.S.S. No. 18 to 40 sieves), the granules are removed, dried, and screened. Oversized material is crushed to produce additional material in the desired range.

UTILITY

The compounds of this invention are useful for control of insects and nematodes.

The compounds also readily control pestiferous insects belonging to such orders as Lepidoptera and Coleoptera. More specifically, insects controlled by the compounds of this invention include southern armyworm (*Spodoptera eridania*), fall armyworm (*Spodoptera*

*frugiperda*), soybea looper (*Pseudoplusia includens*), Mexican bean beetle (*Epilachna varivestis*), tobacco budworm (*Heliothis virescens*) and bollworm (*Heliothis zea*).

The compounds also control pestiferous nematodes, such as the root-knot nematode, *Meloidogyne incognita;* lesion nematode, *Pratylenchus* spp. and dagger nematode, *Xiphinima*.

Insects are normally controlled by applying one or more of the compounds of the instant invention to the locus of infestation, to the area to be protected, or to the pests themselves. For the control of insects on agricultural crops, compounds of this invention are generally applied to the foliage or other plant parts which are infested or which are to be protected. Effective amounts to be applied depend upon the specific compound used, the species to be controlled, its life stage, its size and location, the amount of rainfall, the time of year, moisture, temperature, soil type, percentage of area treated, type of application, plant spacing, and other variables. In general, 0.05 to 10 Kg/ha may be required for insect control in agriculture with rates of 0.15 to 5 Kg/ha usually being sufficient in many situations. In large scale field operations, rates in the range of 0.25 to 3 Kg/ha are generally used.

Nematodes are controlled by applying the compounds of this invention to the locus of infestation, to the area to be protected or to the pests themselves. For the control of nematodes in agricultural crops, a compound of this invention is generally applied to a portion of the plant or surrounding soil which is infested or which is to be protected. Effective amounts to be applied depend upon the specific compound used, the species to be controlled, its life stage, its size and location, the amount of rainfall, the time of year, moisture, temperature, soil type, percentage of area treated, type of application, plant spacing and other variables. In general, 3 to 30 Kg/ha may be required for nematode control in agriculture with rates of 5 to 10 Kg/ha usually being sufficient in many situations.

The compounds of this invention exhibit improved residual insecticidal and nematicidal activity which can reduce the need for closely spaced multiple sprays. This results in greater economy to the grower and dissemination of less insecticide in the environment. An additional advantage is in the reduced side-effects on cotton. Treated leaves tend to remain green and free of reddening.

The compounds of this invention can be mixed with fungicides, bactericides, acaricides, nematicides, insecticides, or other biologically active compounds in order to achieve desired results with a minimum expenditure of time, effort and material. Amounts of these biologically active materials added for each part by weight of the composition of this invention may vary from 0.05 to 25 parts by weight. Suitable agents of this type are well-known to those skilled in the art. Some are listed below:

Fungicides methyl 2-benzimidazolecarbamate (carbendazim)
tetramethylthiuram disulfide (thiuram)
n-dodecylguanidine acetate (dodine)
manganese ethylenebisdithiocarbamate (maneb)
1,4-dichloro-2,5-dimethoxybenzene (chloroneb)
methyl 1-(butylcarbamoyl)-2-benzimidazolecarbamate (benomyl)
2-cyano-N-ethylcarbamoyl-2-methoxyimino acetamide Curzate ®
N-trichloromethylthiotetrahydrophthalimide (captan)
N-trichloromethylthiophthalimide (folpet)

Bactericides tribasic copper sulfate
striptomycin sulfate

Acaricides senecioic acid, ester with 2-sec-butyl-4,6-dinitrophenol (Morocide ®)
6-methyl-1,3-dithiolo[2,3-B]quinonolin-2-one (Morestan ®)
ethyl 4,4' (p-chlorophenyl)-2,2,2-trichloroethanol (Kelthane ®)
bis(pentochloro-2,4-cyclopentadien-lyl) (Pentac ®)
tricyclohexyltin hydroxide (Plictran ®)

Nematicides

2-[diethoxyphosphinylimino]-1,3-dithiethane (Nematak ®)
S-methyl 1-(dimethylcarbamoyl)-N-(methylcarbamoyloxy)thioformimidate (Vydate ®)
S-methyl 1-carbamoyl-N-(methylcarbamoyloxy)thioformidate
N-isopropylphosphoramidic acid, 0-ethyl-0']4-(methylthio)-m-tolyl]diester (Nemacur ®)

Insecticides 3-hydroxy-N-methylcrotonamide(dimethylphosphate)ester (Azodrin ®)
methylcarbamic acid, ester with 2,3-dihydro-2,2-dimethyl-7-benzofuranol (Furadan ®)
0-[2,4,5-trichloro-α-(chloromethyl)-benzyl]phosphoric acid, 0',0'-dimethyl ester (Gardona ®)
2-mercaptosuccinic acid, diethyl ester, S-ester with thionophosphoric acid, dimethyl ester (Malathion ®)
phosphorothioic acid, 0,0-dimethyl, 0-p-nitrophenyl ester (methyl parathion)
methylcarbamic acid, ester with α-naphthol (Sevin ®)
methyl N-[[(methylamino)carbonyl]oxy]ethanimidothioate (methomyl)
N'-(4-chloro-o-tolyl)-N,N-dimethylformamidine (Galecron ®)
0,0-diethyl-0-(2-isopropyl-4-methyl-6-pyrimidylphosphorothioate (Diazinon ®)
octachlorocamphene (toxaphene)
0-ethyl 0-p-nitrophenyl phenylphosphonothioate (EPN)
cyano(3-phenoxyphenyl)-methyl-4-chloro-α-(1-methylethyl)-benzeneacetate (Pydrin ®)
(3-phenoxyphenyl)methyl(+)-cis,trans-3-(2,2-dichloroethenyl)-2,2-dimethylcyclopropanecarboxylate (Ambush ®)
dimethyl N,N'-[thiobis](N-methylimino)carbonyloxy]-bis[ethanimidothioate] Larvin ®)
0-ethyl-S(p-chlorophenyl)ethylphosphonodithioate (Curacron ®)
phosphorothiolothionic acid, 0-ethyl-0-[4-(methylthio)-phenyl]-S-n-propyl ester (Bolstar ®)

EXAMPLE 9

The foliage of red kidney bean plants in the two-leaf stage was sprayed to run-off with dispersions of compounds of this invention at various concentrations. Dispersions were prepared by dissolving appropriately weighed quantities of the active ingredient in 10 ml of acetone and diluting to 100 ml of water containing a surface active agent (Duponol ® L-144 WDG) at 1:3000. After drying, leaves were excised and placed in covered 10 cm petri dishes along with moist filter paper to keep them fresh. Ten southern armyworm larvae were placed in each dish. Tests were run in duplicate. The units were kept in a room maintained at 25°±2° C., 53±5% RH. Results were recorded at the end of 2 days.

| Compound | Concentration % | Mortality % |
|---|---|---|
| 2-[N-methyl-N-[N-methyl-N-[(1-methylthioethylidene)-aminooxycarbonyl]aminothio]-aminocarbonyloxy]benzoic acid butyl ester | .01<br>.005 | 100<br>90 |
| 2-[N-ethyl-N-[N-methyl-N-[(1-methylthioethylidene)-aminooxycarbonyl]aminothio]-aminocarbonyloxy]benzoic acid methyl ester | .01<br>.005 | 95<br>95 |
| Untreated | — | 0 |

EXAMPLE 10

The foliage of red kidney bean plants in the two-leaf stage was sprayed to run-off with dispersions of compounds of this invention at various concentrations. Dispersions were prepared by dissolving appropriately weighed quantities of the active ingredient in 10 ml of acetone and diluting to 100 ml with water containing a surface active agent (Duponol® L-144 WDG) at 1:3000. After drying, plants were placed under artificial light in a room maintained at 25°±2° C., 54±5% RH. After the designated period, leaves were excised and placed in covered 10 cm petri dishes along with moist filter paper to keep them fresh. Ten southern armyworm larvae were placed in each dish. Tests were run in duplicate. The units kept in a room maintained at 25°±2° C., 54±5% RH. Results were recorded at the end of 7 days.

| Compound | Concentration % | Mortality % |
|---|---|---|
| 2-[N-methyl-N-[N-methyl-N-[(1-methylthioethylidene)-aminooxycarbonyl]aminothio]-aminocarbonyloxy]benzoic acid, n-butyl ester | .01<br>.005 | 100<br>95 |
| 2-[N-methyl-N-[N-methyl-N-[(1-methylthioethylidene)-aminooxycarbonyl]) aminothio]-aminocarbonyloxy]benzoic acid, methyl ester | .01<br>.005 | 95<br>85 |
| methyl N-[[(methylamino)carbonyl]oxy]ethanimidothioate (methomyl) | .01<br>.005 | 0<br>0 |
| Untreated | — | 0 |

EXAMPLE 11

Potted cotton plants approximately 25 cm high having 3-4 true leaves were sprayed to run-off with an aqueous dispersion of a compound of this invention at 500 ppm. The sprays contained a surface active agent (Duponol® L-144 WDG) at a concentration of 1:3000. Another set of plants was similarly treated with methomyl. After drying, the plants were set out in the greenhouse and held for observation. Results were recorded after 6 days.

| Compound (500 ppm AI)[1] | Rating[2] (6 days) |
|---|---|
| 2-[N-methyl-N-[N-methyl-N-[(1-methylthioethylidene)aminooxycarbonyl]aminothio]aminocarbonyloxy]benzoic acid n-butyl ester | 0.1 R |
| Methyl N-[[(methylamino)carbonyl]oxy]ethanimidothioate (methomyl) | 4 R |
| Untreated control | 0 |

[1]AI - active ingredient
[2]"R" denotes typical methomyl effect, i.e., reddening of older leaves, slight puckering and black stippling of younger leaves. Rating is on basis of 0 to 10 with 0 indicating no effect and 10 indicating total leaf area involvement.

EXAMPLE 12

Tobacco budworm (*Heliothis virescens*) larvae were treated topically with a compound of this invention. One microliter of each concentration used was applied to the dorso-thoracic area of each larva tested. The stock solutions were prepared by dissolving appropriately weighed quantities of active ingredient in predetermined quantities of acetone. Further diluting with acetone yielded the desired concentrations. Larvae were treated in individual 1-oz. cups in which they were reared on aritificial diet. Fifteen larvae were treated with each desired concentration and kept in a room at 25°±2° C. Results were recorded 2 days after treatment.

| Compound | Concentration (μg/larva) | % Mortality (48 hours) |
|---|---|---|
| 2-[N-methyl-N-[N-methyl-N-[(1-methylthioethylidene)-aminooxycarbonyl]aminothio]aminocarbonyloxy]-benzoic acid, n-butyl ester | 0.5<br>0.25 | 75<br>75 |
| Methyl parathion | 10 | 50 |
| Untreated | — | 0 |

EXAMPLE 13

2-[N-methyl-N-[N-methyl-N-[(1-methylthioethylidene)aminooxycarbonyl]aminothio]aminocarbonyloxy]benzoic acid, methyl ester was dissolved in acetone and mixed into soil containing the root-knot nematode, *Meloidogyne incognita*. The treated soil sample was planted with cucumber seed. After 2 weeks, the roots were examined for nematode injury and the results are summarized below.

| Compound | kg/ha | % Nematode Control |
|---|---|---|
| 2-[N-methyl-N-[N-methyl-N-[(1-methylthioethylidene)-aminooxytcarbonyl]aminothio]aminocarbonyloxy]-benzoic acid, methyl ester | 15 | 100 |
| Untreated control |  | 0 |

What is claimed is:
1. A compound selected from

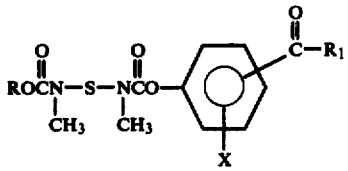 (I)

wherein
R is

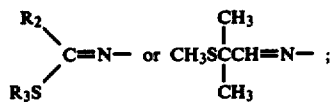

$R_1$ is $OR_4$, $SR_5$ or $NR_6R_7$;
$R_2$ is $C_1$–$C_3$ alkyl, $CH_3OCH_2$— or

$R_3$ is $C_1$–$C_3$ alkyl;
$R_4$ is $C_1$–$C_{14}$ alkyl, —$(CH_2CH_2O)_nR_8$, or $C_6H_5$—;
$R_5$ is $C_1$–$C_4$ alkyl;
$R_6$ and $R_7$ are independently H or $C_1$–$C_3$ alkyl;
$R_8$ is H or $C_1$–$C_3$ alkyl;
X is H, $C_1$–$C_9$ alkyl, Cl, $(CH_3)_2N$ or $OR_9$;
$R_9$ is $C_1$–$C_4$ alkyl;
n is 1, 2 or 3.

2. A compound of claim 1 wherein R is

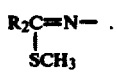

3. A compound of claim 1 wherein $R_2$ is $C_1$–$C_3$ alkyl.
4. A compound of claim 2 wherein $R_2$ is $CH_3$.
5. A compound of claim 1 wherein $R_1$ is $OR_4$.
6. A compound of claim 1 wherein the

group is in the 2-position of the aromatic ring.
7. A compound of claim 1 wherein $R_4$ is $C_1$–$C_4$ alkyl or —$(CH_2CH_2O)_nR_8$.
8. A compound of claim 1 wherein X is H.
9. A compound of claim 1 wherein R is

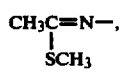

$R_1$ is $OR_4$, $R_4$ is $C_1$–$C_4$ alkyl or —$(CH_2CH_2O)_nR_8$, X is H, and

is in the 2-position of the aromatic ring.
10. The compound of claim 1 which is 2-[N-methyl-N-[N-methyl-N-[(1-methylthioethylidene)aminooxycarbonyl]aminothio]aminocarbonyloxy]benzoic acid butyl ester.
11. The compound of claim 1 which is 2-[N-methyl-N-[N-methyl-N-[(1-methylthioethylidene)aminooxycarbonyl]aminothio]aminocarbonyloxy]benzoic acid methyl ester.
12. A composition suitable for control of pestiferous insects comprising an insecticidally effective amount of a compound of claim 1 and at least one of (a) a diluent and (b) a surfactant.
13. A composition suitable for control of pestiferous insects comprising an insecticidally effective amount of a compound of claim 2 and at least one of (a) a diluent and (b) a surfactant.
14. A composition suitable for control of pestiferous insects comprising an insecticidally effective amount of a compound of claim 3 and at least one of (a) a diluent and (b) a surfactant.
15. A composition suitable for control of pestiferous insects comprising an insecticidally effective amount of a compound of claim 4 and at least one of (a) a diluent and (b) a surfactant.
16. A composition suitable for control of pestiferous insects comprising an insecticidally effective amount of a compound of claim 5 and at least one of (a) a diluent and (b) a surfactant.
17. A composition suitable for control of pestiferous insects comprising an insecticidally effective amount of a compound of claim 6 and at least one of (a) a diluent and (b) a surfactant.
18. A composition suitable for control of pestiferous insects comprising an insecticidally effective amount of a compound of claim 7 and at least one of (a) a diluent and (b) a surfactant.
19. A composition suitable for control of pestiferous insects comprising an insecticidally effective amount of a compound of claim 8 and at least one of (a) a diluent and (b) a surfactant.
20. A composition suitable for control of pestiferous insects comprising an insecticidally effective amount of a compound of claim 9 and at least one of (a) a diluent and (b) a surfactant.
21. A composition suitable for control of pestiferous insects comprising an insecticidally effective amount of the compound of claim 10 and at least one of (a) a diluent and (b) a surfactant.
22. A composition suitable for control of pestiferous insects comprising an insecticidally effective amount of the compound of claim 11 and at least one of (a) a diluent and (b) a surfactant.
23. A composition suitable for control of pestiferous nematodes comprising a nematicidally effective amount of a compound of claim 1 and at least one of (a) a diluent and (b) a surfactant.
24. A composition suitable for control of pestiferous nematodes comprising a nematicidally effective amount of a compound of claim 2 and at least one of (a) a diluent and (b) a surfactant.
25. A composition suitable for control of pestiferous nematodes comprising a nematicidally effective amount of a compound of claim 3 and at least one of (a) a diluent and (b) a surfactant.
26. A composition suitable for control of pestiferous nematodes comprising a nematicidally effective amount of a compound of claim 4 and at least one of (a) a diluent and (b) a surfactant.
27. A composition suitable for control of pestiferous nematodes comprising a nematicidally effective amount of a compound of claim 5 and at least one of (a) a diluent and (b) a surfactant.

28. A composition suitable for control of pestiferous nematodes comprising a nematicidally effective amount of a compound of claim 6 and at least one of (a) a diluent and (b) a surfactant.

29. A composition suitable for control of pestiferous nematodes comprising a nematicidally effective amount of a compound of claim 7 and at least one of (a) a diluent and (b) a surfactant.

30. A composition suitable for control of pestiferous nematodes comprising a nematicidally effective amount of a compound of claim 8 and at least one of (a) a diluent and (b) a surfactant.

31. A composition suitable for control of pestiferous nematodes comprising a nematicidally effective amount of a compound of claim 9 and at least one of (a) a diluent and (b) a surfactant.

32. A composition suitable for control of pestiferous nematodes comprising a nematicidally effective amount of the compound of claim 10 and at least one of (a) a diluent and (b) a surfactant.

33. A composition suitable for control of pestiferous nematodes comprising a nematicidally effective amount of the compound of claim 11 and at least one of (a) a diluent and (b) a surfactant.

34. A method for control of pestiferous insects which comprises applying to a locus of infestation, to the area to be protected or to the pests themselves an insecticidally effective amount of a compound of claim 1.

35. A method for control of pestiferous insects which comprises applying to a locus of infestation, to the area to be protected or to the pests themselves an insecticidally effective amount of a compound of claim 2.

36. A method for control of pestiferous insects which comprises applying to a locus of infestation, to the area to be protected or to the pests themselves an insecticidally effective amount of a compound of claim 3.

37. A method for control of pestiferous insects which comprises applying to a locus of infestation, to the area to be protected or to the pests themselves an insecticidally effective amount of a compound of claim 4.

38. A method for control of pestiferous insects which comprises applying to a locus of infestation, to the area to be protected or to the pests themselves an insecticidally effective amount of a compound of claim 5.

39. A method for control of pestiferous insects which comprises applying to a locus of infestation, to the area to be protected or to the pests themselves an insecticidally effective amount of a compound of claim 6.

40. A method for control of pestiferous insects which comprises applying to a locus of infestation, to the area to be protected or to the pests themselves an insecticidally effective amount of a compound of claim 7.

41. A method for control of pestiferous insects which comprises applying to a locus of infestation, to the area to be protected or to the pests themselves an insecticidally effective amount of a compound of claim 8.

42. A method for control of pestiferous insects which comprises applying to a locus of infestation, to the area to be protected or to the pests themselves an insecticidally effective amount of a compound of claim 9.

43. A method for control of pestiferous insects which comprises applying to a locus of infestation, to the area to be protected or to the pests themselves an insecticidally effective amount of the compound of claim 10.

44. A method for control of pestiferous insects which comprises applying to a locus of infestation, to the area to be protected or to the pests themselves an insecticidally effective amount of the compound of claim 11.

45. A method for control of pestiferous nematodes which comprises applying to a locus of infestation, to the area to be protected or to the pests themselves a nematicidally effective amount of a compound of claim 1.

46. A method for control of pestiferous nematodes which comprises applying to a locus of infestation, to the area to be protected or to the pests themselves a nematicidally effective amount of a compound of claim 2.

47. A method for control of pestiferous nematodes which comprises applying to a locus of infestation, to the area to be protected or to the pests themselves a nematicidally effective amount of a compound of claim 3.

48. A method for control of pestiferous nematodes which comprises applying to a locus of infestation, to the area to be protected or to the pests themselves a nematicidally effective amount of a compound of claim 4.

49. A method for control of pestiferous nematodes which comprises applying to a locus of infestation, to the area to be protected or to the pests themselves a nematicidally effective amount of a compound of claim 5.

50. A method for control of pestiferous nematodes which comprises applying to a locus of infestation, to the area to be protected or to the pests themselves a nematicidally effective amount of a compound of claim 6.

51. A method for control of pestiferous nematodes which comprises applying to a locus of infestation, to the area to be protected or to the pests themselves a nematicidally effective amount of a compound of claim 7.

52. A method for control of pestiferous nematodes which comprises applying to a locus of infestation, to the area to be protected or to the pests themselves a nematicidally effective amount of a compound of claim 8.

53. A method for control of pestiferous nematodes which comprises applying to a locus of infestation, to the area to be protected or to the pests themselves a nematicidally effective amount of a compound of claim 9.

54. A method for control of pestiferous nematodes which comprises applying to a locus of infestation, to the area to be protected or to the pests themselves a nematicidally effective amount of the compound of claim 10.

55. A method for control of pestiferous nematodes which comprises applying to a locus of infestation, to the area to be protected or to the pests themselves a nematicidally effective amount of the compound of claim 11.

* * * * *